United States Patent
Moore et al.

(10) Patent No.: US 9,416,345 B2
(45) Date of Patent: Aug. 16, 2016

(54) COLD BOX WITH A RACK LOADED WITH TUBE-SHAPED VESSELS FOR AUTOMATED FILLING BY AN AUTOMATED PIPETTING DEVICE

(71) Applicant: CyBio AG, Jena (DE)

(72) Inventors: Thomas Moore, Jena (DE); Michael Kiehntopf, Jena (DE)

(73) Assignee: Analytik Jena AG, Jena (DE)

( * ) Notice: Subject to any disclaimer, the term of this patent is extended or adjusted under 35 U.S.C. 154(b) by 260 days.

(21) Appl. No.: 14/174,038

(22) Filed: Feb. 6, 2014

(65) Prior Publication Data

US 2014/0216059 A1 Aug. 7, 2014

(30) Foreign Application Priority Data

Feb. 6, 2013 (DE) .................. 10 2013 101 176

(51) Int. Cl.
 *F25B 21/02* (2006.01)
 *C12M 1/00* (2006.01)
 *B01L 7/00* (2006.01)

(52) U.S. Cl.
 CPC ........ *C12M 45/20* (2013.01); *B01L 7/00* (2013.01); *B01L 2200/141* (2013.01); *B01L 2300/045* (2013.01); *B01L 2300/049* (2013.01); *B01L 2300/0829* (2013.01); *B01L 2300/1822* (2013.01); *B01L 2300/1838* (2013.01); *B01L 2300/1883* (2013.01); *B01L 2300/1894* (2013.01); *B01L 2400/0644* (2013.01)

(58) Field of Classification Search
 CPC ........... C12M 45/20; B01L 2300/1894; B01L 2300/049; B01L 2300/1822; B01L 2300/1838; B01L 2300/045; B01L 2300/1883; B01L 2400/0644; B01L 2200/141; B01L 3/02
 See application file for complete search history.

(56) References Cited

U.S. PATENT DOCUMENTS

| 4,919,894 A | 4/1990 | Daniel |
| 4,950,608 A * | 8/1990 | Kishimoto ............... B01L 7/52 165/104.24 |
| 5,689,970 A | 11/1997 | Chopas |

(Continued)

FOREIGN PATENT DOCUMENTS

| DE | 39 30801 A1 | 3/1991 |
| DE | 198 24 117 A1 | 12/1998 |

(Continued)

OTHER PUBLICATIONS

Gill, G.B., et al., "Guidelines for Handling Air-Sensitive Compounds", Aldrichimice Acta 1986, 19(2):31-41.

*Primary Examiner* — Emmanuel Duke
(74) *Attorney, Agent, or Firm* — Duane Morris LLP (57) ABSTRACT

A cold box having a cooling receptacle filled with a dry protective gas in which is accommodated a rack loaded with tube-shaped vessels. The cooling receptacle is covered by a movable lid which is associated with a lid part and which is preferably formed by an outer lid and a rotatable inner lid integrated in the outer lid so that the cooling receptacle is completely covered in every position of the lid. At least one of the through-holes provided in the inner lid can be arranged over a respective tube-shaped vessel by a coordinated movement of the outer lid and rotation of the inner lid so that the tube-shaped vessel located under the through-hole in alignment therewith can be filled with a sample through the through-hole by means of a commercially available pipette tip/dispensing needle of an automated pipetting device.

4 Claims, 10 Drawing Sheets

(56) References Cited

U.S. PATENT DOCUMENTS

| | | | | |
|---|---|---|---|---|
| 5,792,430 A * | 8/1998 | Hamper | ............... | B01J 19/0046 422/116 |
| 5,863,507 A * | 1/1999 | James | ............... | B01L 7/00 422/562 |
| 6,141,975 A | 11/2000 | Tatsumi | | |
| 6,170,267 B1 * | 1/2001 | Kitaoka | ............... | B01L 7/00 62/3.6 |
| 6,337,435 B1 * | 1/2002 | Chu | ............... | B01L 7/52 136/203 |
| 6,341,490 B1 * | 1/2002 | Jones | ............... | B01L 3/50851 165/80.3 |
| 6,696,302 B1 | 2/2004 | Franzen | | |
| 7,036,667 B2 * | 5/2006 | Greenstein | ............... | B01L 9/527 206/205 |
| 7,452,510 B2 * | 11/2008 | Weinfield | ............... | B01D 61/18 141/130 |
| 2002/0132356 A1 | 9/2002 | Qureshi et al. | | |
| 2003/0143120 A1 * | 7/2003 | Ruediger | ............... | B01L 19/0046 422/561 |
| 2004/0023371 A1 * | 2/2004 | Fawcett | ............... | B01L 7/52 435/303.1 |
| 2004/0028562 A1 * | 2/2004 | Greve | ............... | B01J 19/0093 422/545 |
| 2005/0211622 A1 * | 9/2005 | Carlson | ............... | B01J 19/0046 210/428 |
| 2006/0093530 A1 * | 5/2006 | Ueda | ............... | B01L 9/543 422/400 |
| 2008/0072689 A1 | 3/2008 | Muraishi et al. | | |
| 2009/0130745 A1 * | 5/2009 | Williams | ............... | B01L 3/5027 435/287.2 |
| 2010/0258578 A1 * | 10/2010 | Motadel | ............... | B01L 9/543 221/1 |
| 2011/0236278 A1 * | 9/2011 | Motadel | ............... | B01L 9/543 422/560 |
| 2011/0293488 A1 * | 12/2011 | Nichols | ............... | B01L 3/50853 422/500 |
| 2012/0295249 A1 * | 11/2012 | Cherubini | ............... | G01N 21/645 435/5 |
| 2012/0329143 A1 | 12/2012 | Yamazaki et al. | | |
| 2013/0240181 A1 * | 9/2013 | Yasunaga | ............... | F28D 15/00 165/104.28 |

FOREIGN PATENT DOCUMENTS

| | | |
|---|---|---|
| DE | 10 2004 008 496 B3 | 7/2005 |
| EP | 1 898 218 A2 | 3/2008 |
| JP | 2009-139269 A | 6/2009 |
| WO | WO 2005/085092 A3 | 9/2005 |

* cited by examiner

Fig. 8 though vessels are also possible (other body fluids or dissolved biochemical samples, also separate from any solvents that may be needed).

COLD BOX WITH A RACK LOADED WITH TUBE-SHAPED VESSELS FOR AUTOMATED FILLING BY AN AUTOMATED PIPETTING DEVICE

RELATED APPLICATIONS

The present application claims priority benefit of German Application No. DE 10 2013 101 176.4 filed on Feb. 6, 2013, the contents of which are incorporated by reference in its entirety.

FIELD OF THE INVENTION

Blood samples or other biological specimens are routinely analyzed in laboratory practice. It is of interest to analyze these samples while still fresh, but also to examine them again at a later time for other analyses or for comparative studies. The samples often arrive irregularly over a given period of time (e.g., urgent samples, higher-than-average quantities of samples after morning collections, send-in samples) so that it is usually impossible to examine the samples continuously in an equally fresh condition. It is well known that the quality of samples suffers when stored at room temperature, i.e., laboratory results which were determined directly from a fresh sample do not necessarily correspond to results from the same sample after longer storage. Important data is lost through improper storage. It is well known that the quality of samples can be preserved by cooling the samples or storing them at low temperatures. Biobanks in which samples are stored for decades at nitrogen temperature are illustrative of this.

BACKGROUND OF THE INVENTION

In practice, several thousand samples pass through state-of-the-art automated laboratory installations every day. With the help of laboratory management software, these samples are managed and sent to the appropriate test equipment according to the requested diagnostic tasks, and the test results are archived and sent out. Samples intended for later use can easily be sequestered out of this process. Thus far, however, there has been no simple possibility for suitably dividing these samples into portions (aliquoting) as quickly as possible (above all in an automated manner) and cooling them to a suitable storage temperature as soon as possible.

Aliquoting is usually carried out by means of automated pipetting devices which detect (compare to the database) the sample tubes in which the samples arrive at the laboratory and which are labeled with bar codes, take up (suction, aspirate) the samples by means of pipette tips or dispensing needles of an automated pipetting device and divide them into aliquots (fractions of the sample) by distributing them to a plurality of tube-shaped vessels which are suitable for freezing and which are likewise coded. Commonly used sampling tubes are manufactured by Sarstedt, e.g., Monovette®, and BD, e.g. Vacutainer®.

Tube-shaped vessels (crytotubes with two-dimensional bar codes) manufactured by Thermo Matrix, Thermo Scientific, ABgene or FluiX, for example, are used for the aliquots. These tube-shaped vessels are in turn usually supplied in plastic racks (tube racks) in 8×12 format (eight rows A-H and twelve columns, 1-12).

The aliquots are often 1-ml portions of the serum supernatant of the samples. However, other components of a blood sample or completely different biological samples are also possible (other body fluids or dissolved biochemical samples, also separate from any solvents that may be needed).

Four temperature ranges are considered practical to employ for the processing and storage of samples. Fast processing of liquid samples at room temperature, intermediate storage at −20° C. for the space of a few hours, storage at −80° C. for many weeks and months, and indefinite storage under actual cryogenic conditions, i.e., in liquid nitrogen at 77° K. In routine laboratory practice, this is often carried out in stages. Accordingly, insertion into the −80° C. area of an automatic storage is often carried out via a −20° C. interface system (e.g., Liconic ULT Store). A cold box according to the invention serves as −20° C. intermediate storage and is used irrespective of the further use of the sample.

In current practice, the tube-shaped vessels with the samples which often arrive in the laboratory at indeterminate times are filled at room temperature and are loaded into a rack so that the rack is completely filled before inserting it into a cooling device or the rack is placed in a cassette having a plurality of places for the racks, and the cassette which is completely filled with racks is then inserted into a cooling device, e.g., the STT3k0-DF by Liconic AG. The individual samples are exposed to room temperature for various lengths of time before being inserted into the cooling devices, which leads to a loss of quality as was mentioned above.

It is the object of the invention to find a solution by which samples arriving in a laboratory at different times and in different quantities can be cooled to a cooling temperature within a very short time.

The object of the invention is met by a cold box with a rack loaded with tube-shaped vessels for automated filling by an automated pipetting device. This cold box has a bottom part and a lid part, a rack which is loaded with tube-shaped vessels in a matrix of rows and columns, wherein the rows extend along the width of the rack and the columns extend along the length of the rack, a cooling receptacle which is enclosed by thermal insulation and which is at least partially arranged in the bottom part and which is adapted to the outer dimensions of the loaded rack, and in which the loaded rack is placed.

The lid part comprises a lid frame and a lid which is movable in the lid frame in direction of the columns or rows of the rack and in which is provided a quantity of openings which are adapted to the circumference size of a commercially available pipette tip/dispensing needle of an automated pipetting device so that one of the openings can be positioned over each individual tube-shaped vessel in the rack. The lid completely covers the cooling receptacle in every position so that a dry protective gas with which the cooling receptacle is filled and which is heavier than air remains in the cooling receptacle. The cold box further has a cooling device which is integrated in the thermal insulation in the bottom part and which contacts the cooling receptacle.

The lid is advantageously formed of an outer lid with a cutout which reaches at least over the length of a column and an inner lid which is adjustable relative to the outer lid and which covers the cutout. The at least one opening is a through-hole in the inner lid and can be positioned with respect to the tube-shaped vessels by moving the outer lid and adjusting the inner lid.

It is advantageous when the cooling receptacle is located partly in the bottom part and partly in the lid part, and the portion of the cooling receptacle in the lid part is formed by a formation in the thermal insulation and the portion of the cooling receptacle in the bottom part is formed by a trough. The rack advantageously sits on a tray with two tray handles for easy insertion and removal of the rack. Two opposing recesses are provided in the formation of the thermal insulation for the tray handles, and the tray handles are received in these recesses.

To fill the cooling receptacle, it is advantageous to provide a feed line for the protective gas in the bottom part. The cooling device advantageously comprises a plate-shaped Peltier cooler and a liquid circulating cooler. The Peltier cooler communicates directly with the trough on the one hand and with the liquid circulating cooler on the other hand. In order for the lid to completely cover the cooling receptacle in every position, this lid is movable proceeding from a central position in positive or negative direction by one half of the length of the rack between two end positions and the length of the lid is selected correspondingly. The inner lid is advantageously integrated in the outer lid. The outer lid and the inner lid can also be arranged one above the other so as to overlap.

In a preferred embodiment form of the cold box, the inner lid is round and is rotatable by at least 180° around the geometric center of the outer lid, and the quantity of through-holes is equivalent to one half of the quantity of tube-shaped vessels arranged in a row, the through-holes being arranged on a straight line radial to the center of the outer lid. In order to be able to monitor the fill level, it is advantageous to provide a gas sensor in the cooling receptacle.

BRIEF DESCRIPTION OF THE DRAWINGS

The cold box will be described in more detail in the following based on embodiment examples referring to the drawings. The drawings show.

DESCRIPTION THE EMBODIMENTS

A cold box 1 according to the invention with a rack 3 loaded with tube-shaped vessels 2 for automated filling by means of an automated pipetting device 15 substantially comprises a rack 3 loaded with tube-shaped vessels 2, a cooling receptacle 5 filled with dry protective gas 4, a cooling device 10 and a lid 12 which closes the cooling receptacle 5 and is movable in a lid frame 7.1.

Figure 4:
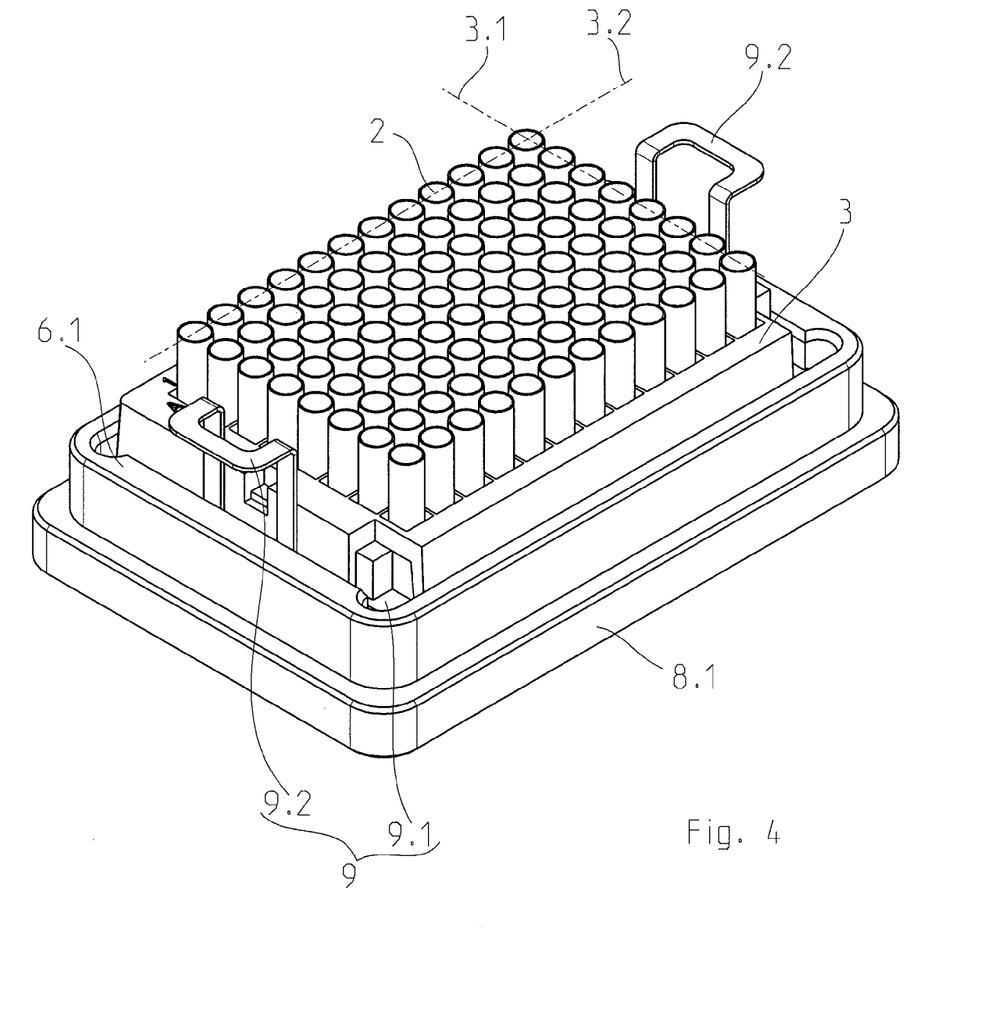
FIG. 4 is a bottom part of a cold box with thermal insulation partly removed.

In the rack 3 which is loaded with tube-shaped vessels 2, clearly shown in FIG. 4, the tube-shaped vessels 2 are arranged in a matrix of rows 3.1 and columns 3.2. The rows 3.1 extend along the width of the rack 3 and the columns 3.2 extend along the length of the rack 3. Racks 3 of this type are known from the art. They have standardized outer dimensions and usually have eight places for tube-shaped vessels 2 arranged in a row 3.1 and twelve places for tube-shaped vessels 2 arranged in a column 3.2. By virtue of their arrangement in rows 3.1 to which letters (A . . . H) are assigned in alphabetic order and columns 3.2 to which natural numbers (1 . . . 12) are assigned consecutively, the location of each tube-shaped vessel 2 is uniquely defined by a row 3.1 and a column 3.2, which allows a through-hole 7.3.1, described later, to be specifically positioned so as to be aligned over each tube-shaped vessel 2 for guiding through a pipette tip or dispensing needle 16 of an automated pipetting device 15. The outer dimensions of a rack 3 which is loaded with tube-shaped vessels 2 are determined with respect to width and length by the rack 3 itself. Conversely, the height is substantially determined by the length of the tube-shaped vessels 2, although the latter can also be supplied in standardized lengths.

The cooling receptacle 5 is adapted to the outer dimensions, length, width and height, of the loaded rack 3; that is, its inner dimensions are only negligibly larger in order to prevent tilting of the rack 3 when inserting into or removing from the cooling receptacle 5. The interior which is enclosed by the cooling receptacle 5 and which determines the interior volume to be cooled is accordingly minimized in an advantageous manner. As was mentioned in the introductory part, the cold box 1 is to be used for cooling samples to −20° C. The cooling receptacle 5 is closed by the lid 12, formed in this case by an outer lid 7.2 and an inner lid 7.3 integrated therein. As will be described later, at least one through-hole 7.3.1 is provided in the inner lid 7.3. In order to prevent air from entering the cooling receptacle 5 through this at least one through-hole 7.3.1 and thus forming ice inside the cooling receptacle 5 as a result of condensation and subsequent freezing of the condensation, the cooling receptacle 5 is filled with a protective gas 4. Protective gas 4 which is heavier than air, in particular argon, is used for this purpose. A feed line 4.1 through which the closed cooling receptacle 5 is filled with protective gas 4 is provided for filling the cooling receptacle 5. A gas sensor 11 is advantageously provided in the cooling receptacle 5 for detecting the fill level of the cooling receptacle 5.

Although the inner volume of the cooling receptacle 5 permanently communicates with the atmosphere via at least one opening 13, in particular a through-hole 7.3.1, at least in this first embodiment form as will be described later, no air can penetrate into the cooling receptacle 5 due to its being filled with the protective gas 4, or the penetration of air is largely prevented in this way. Of course, it would also be possible to always cover this at least one through-hole 7.3.1 and to remove the cover only when the tube-shaped vessels 2 are to be filled through the at least one through-hole 7.3.1 as will be described later. However, a solution of this kind would mean additional mechanical expenditure and control resources and does not prevent air from penetrating nearly as effectively as the protective gas 4.

In order to insert the rack 3 which is loaded with tube-shaped vessels 2 into the cooling receptacle 5, the cold box 1 is divided into a bottom part 6 and a removable lid part 7 which are connected to one another, i.e., which integrate the closed cooling receptacle 5 in the closed state of the cold box 1.

In particular for convenient handling of the filled rack 3 when inserting and removing, the cooling receptacle 5 is advantageously not accommodated in its entirety in the bottom part 6 and is only covered by placing the lid part 7 on top; rather, the cooling receptacle 5 is formed of a portion 5.1 in the lid part and a portion 5.2 in the bottom part. The portion 5.2 of the cooling receptacle in the bottom part which comprises a cooling receptacle bottom and approximately 80% of the height of four sides walls of the cooling receptacle is at least partially constructed as a trough 6.1. The trough 6.1 is made of a material with good thermal conductivity and a high thermal capacity. Aluminum is preferably used for this purpose, although other metals or even modern plastics can be used. The trough 6.1 is enclosed on all sides, advantageously by only a first portion of the thermal insulation 8. This first portion of the thermal insulation 8 is advantageously a first shaped body 8.1 whose outer circumference and shape characterize the shape and size of the bottom part 6 of the cold box 1.

In order to be able to set the lid part 7 on the bottom part 6 so as to effect a positive engagement which ensures that they will be positioned relative to one another in a definite manner, the first shaped body 8.1 advantageously projects beyond the trough 6.1 and is stepped toward the outer side so that it encloses a larger free inner cross section compared to the trough 6.1.

The lid part 7 substantially comprises a lid frame 7.1, a lid 12 which is movable in the lid frame 7.1 and which has at least one through-hole 7.3.1 adapted to the circumference size of a commercially available pipette tip/dispensing needle 16 of an automated pipetting device 15. According to a first embodiment example shown in FIGS. 1 to 4, the lid 12 is formed of an outer lid 7.2 and a rotatable inner lid 7.3 which is integrated in the outer lid 7.2.

The lid frame 7.1 is reinforced at the underside facing the bottom part 6 by a second portion of the thermal insulation 8 which is formed as a second shaped body 8.2. The outer circumferential shape and circumferential size of the second shaped body 8.2 corresponds to the outer circumferential shape and circumferential size of the first shaped body 8.1. It is stepped circumferentially toward the inner side such that a positive engagement is brought about between bottom part 6 and lid part 7 when the lid part 7 is placed on the bottom part 6. The portion 5.1 of the cooling receptacle in the lid part is formed by a formation 8.3 in the second shaped body 8.2. The formation 8.3 advantageously has a free inner cross section equal to the outer cross section of the trough 6.1. Two opposing recesses 8.4 are advantageously provided in the second shaped body 8.2 to provide space for two tray handles 9.2 of a tray 9.

For a convenient and secure handling of the loaded rack 3, particularly when inserting it into or removing it from the cold box 1, this rack 3 is advantageously accommodated on a tray 9 standing in the cooling receptacle 5. The tray 9 has a frame-shaped tray base 9.1 adapted in size to the rack 3 and lateral tray handles 9.2.

Figure 1A:
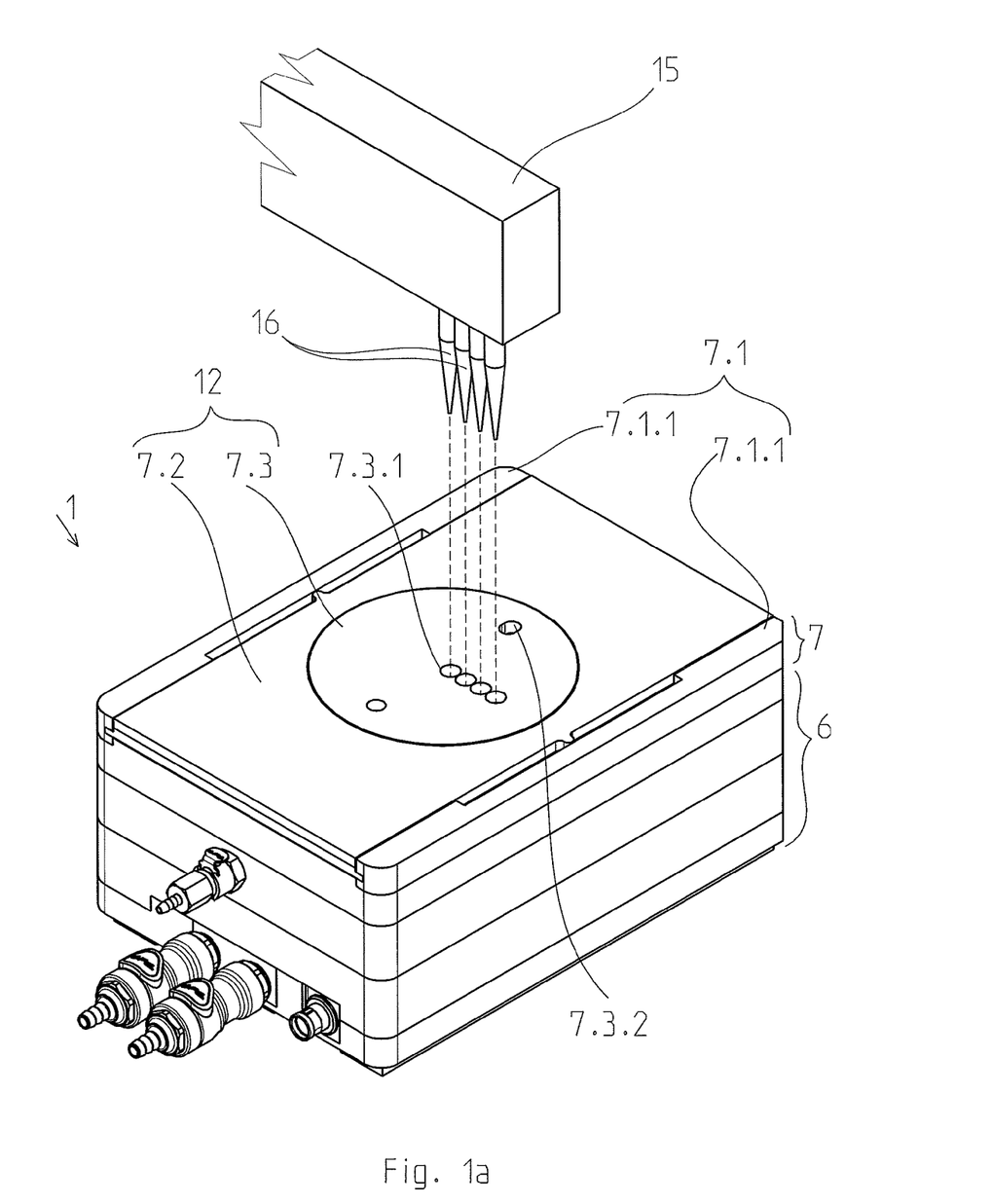
FIG. 1a is a first embodiment example of a cold box in which the lid is located in a central position.
Figure 1B:
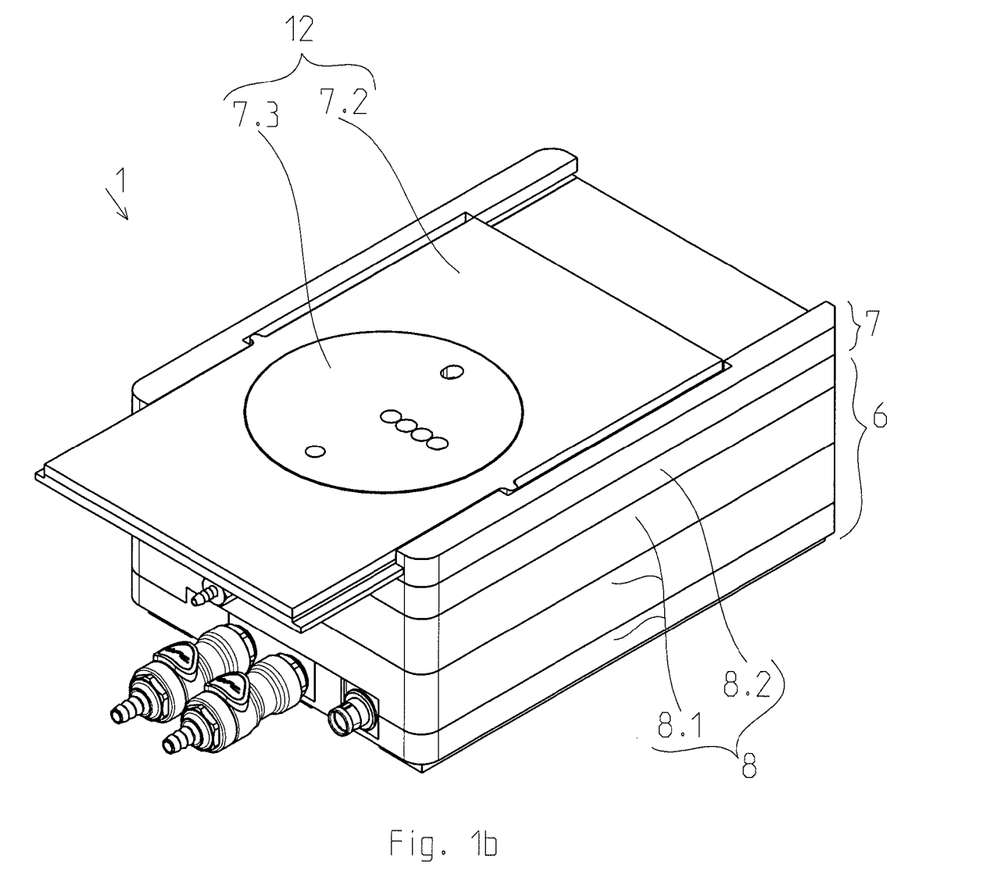
FIG. 1b is the cold box according to FIG. 1 in which the lid is located in one of two end positions.
Figure 2:
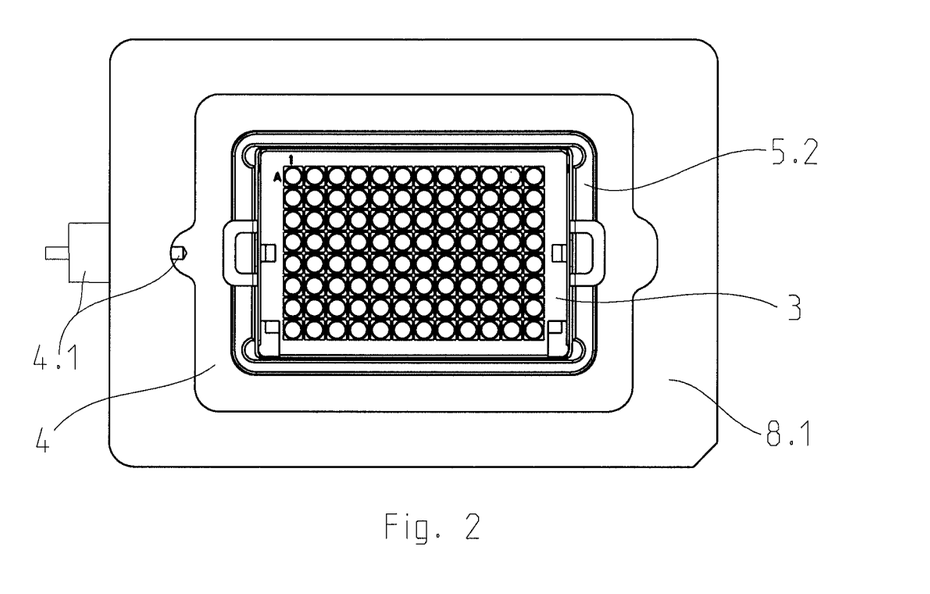
FIG. 2 is a top view of a cold box without a lid part.

The lid frame 7.1 has two parallel frame parts 7.1.1 between which the outer lid 7.2 is movable in direction of the columns 3.2 of the filled rack 3 proceeding from a central position (see FIG. 1a) in positive and negative direction between two end positions (see, e.g., FIG. 1b). The possible movement path is advantageously equal to one half of the length of the rack 3. The length of the outer lid 7.2 is selected in such a way that the cooling receptacle 5 also remains completely covered by the outer lid 7.2 and the inner lid 7.3 in the end positions.

According to the first embodiment example shown in FIGS. 1 to 4, the inner lid 7.3 is round and is rotatable inside the outer lid 7.2 by at least 180° around the geometric center of the outer lid 7.2. A quantity of through-holes 7.3.1 equivalent to one half of the quantity of tube-shaped vessels 2 arranged in a row 3.1 is provided in the inner lid 7.3 along a straight line extending radial to the center. Accordingly, there are four through-holes 7.3.1 in a rack 3 with 8×12 tube-shaped vessels 2. Their spacing is adapted to the spacing of the axes of symmetry of the tube-shaped vessels 2 so that the four through-holes 7.3.1 can be positioned above tube-shaped vessels 2 arranged along a half-row 3.1 so as to be aligned with them. The through-holes 7.3.1 are advantageously as small as possible and as large as necessary for the insertion of commercially available pipette tips/dispensing needles 16. A through-hole 7.3.1 can be positioned so as to be aligned with each tube-shaped vessel 2 through a combination of movement of the outer lid 7.2 and rotation of the inner lid 7.3.

To automate the movement and rotation, at least one coupling element 7.3.2 is advantageously provided off-center at the inner lid 7.3, and an externally controlled and driven gripper can be connected to the inner lid 7.3 by means of this at least one coupling element 7.3.2. By means of the connected gripper, a rotational movement can be directly initiated in the inner lid 7.3 and a feed movement can be indirectly initiated in the outer lid 7.2 so that the at least one through-hole 7.3.1 can be positioned over each individual tube-shaped vessel 2 in the rack 3 by the movement of the outer lid 7.2 and the adjustment of the inner lid 7.3. The gripper can be secured, for example, to a portal spanning a large area of the laboratory and can be used simultaneously for a plurality of cold boxes 1 according to the invention.

The controlling means and the drives corresponding to the movement can also be provided at the cold box 1 itself. However, this would make the cold box 1 substantially more expensive, more prone to breakdown, heavier and less manageable. In principle, the cold box 1 can also be operated manually. Positioning of the inner lid and outer lid can also be carried out by means of a shaft provided at the automated pipetting device 15 for receiving pipette tips 16.

The idea upon which the cold box is based also allows the through-holes 7.3.1 to be formed large enough that the tube-shaped vessels 2 can be inserted through them into the cold box and can be deposited specifically in the individual spaces in the rack 3. However, constructing and using the cold box 1 in this way has the drawback that not only the sample, which is generally at room temperature, but also the tube-shaped vessels 2 must be inserted into the cooling receptacle 5 and cooled down. Therefore, cooling takes longer and there is a substantially greater risk that the protective gas 4 will partially escape via the through-holes 7.3.1 and that air will penetrate, which can happen particularly in case of shaking of the cooling receptacle 5 causing turbulence in the protective gas 4 and drafts in the laboratory. In this case, substantial advantages afforded by the cold box 1 according to the invention would be forfeited.

Owing to the fact that only pipette tips/dispensing needles 16 are inserted briefly and also only partially into the cooling receptacle 5, the temperature inside the cooling receptacle 5 does not change or does not measurably change. The sample is dispensed into the tube-shaped vessels 2 which have already been cooled beforehand to the desired temperature so that an extremely fast cooling of the sample takes place within a few minutes.

Figure 5:
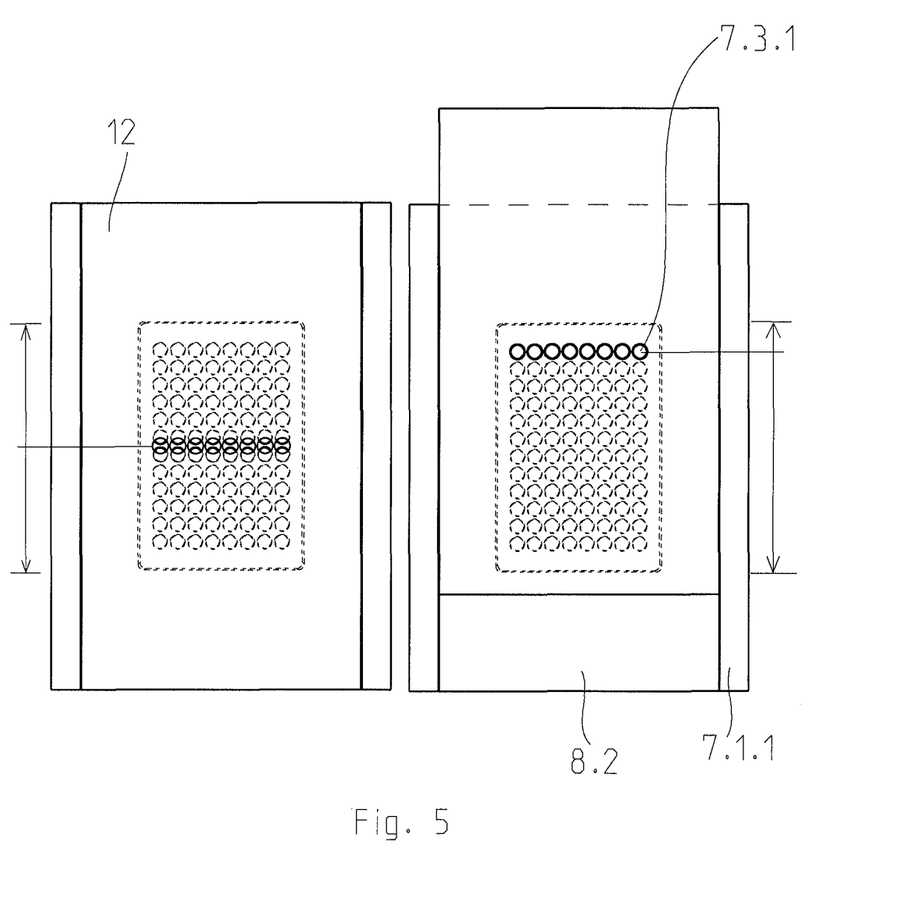
FIG. 5 is a lid part of a cold box according to a second embodiment example in two different positions.

Various embodiment examples of the lid 12 are shown in the following. In the most simple variant, the lid 12 according to a second embodiment example shown in FIG. 5 is constructed in one part and has a series of through-holes 7.3.1 in a quantity equal to the quantity of columns 3.2, e.g., eight, which are arranged on a straight line perpendicular to the moving direction of the lid 12. In an inferior embodiment, a slot could be provided instead of through-holes 7.3.1. The lid 12 is movable from a central position in two directions to an end position so that the series of through-holes 7.3.1 can be positioned successively over all rows 3.1. Here again, as in the first embodiment example and the embodiment examples to be described later, the cooling receptacle 5 remains closed by means of the lid part 7. The series of through-holes 7.3.1 is advantageously located in the end positions above the second shaped body 8.2 so that the cold box 1 is tightly closed in these positions, i.e., there is no longer communication with the atmosphere via the through-holes 7.3.1. In this case, the lid 12 and the second shaped body 8.2 and the possible movement path must be longer than the length of the columns.

Figure 6:
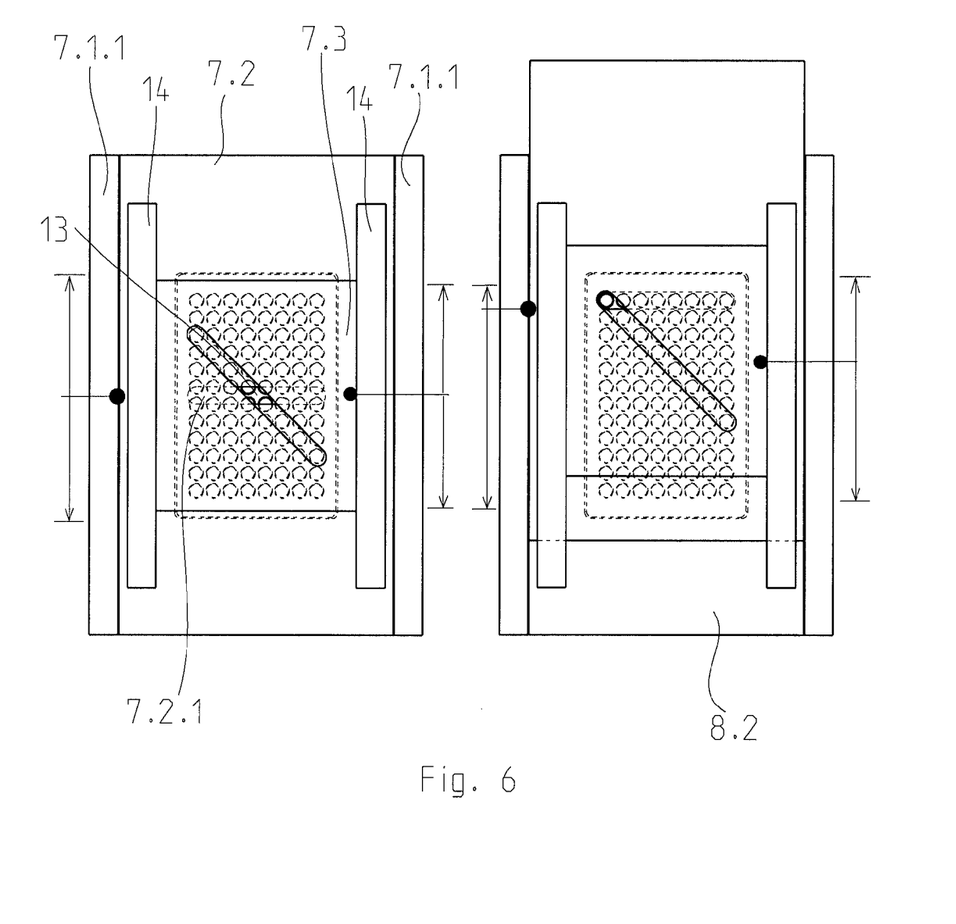
FIG. 6 is a lid part of a cold box according to a third embodiment example in two different positions.

According to a third embodiment example shown in FIG. 6, the inner lid 7.3 can be moved in the same direction as the outer lid 7.2 so as to be guided on the outer lid 7.2 in guide rails 14. A diagonally running slot which overlaps with a slot-shaped cutout 7.2.1 in the outer lid 7.2 and releases an opening 13 moving in direction of row 3.1 is provided in the inner lid 7.3. Instead of the slot, a series of through-holes 7.3.1 could also be advantageously provided in the inner lid 7.3.

Figure 7:
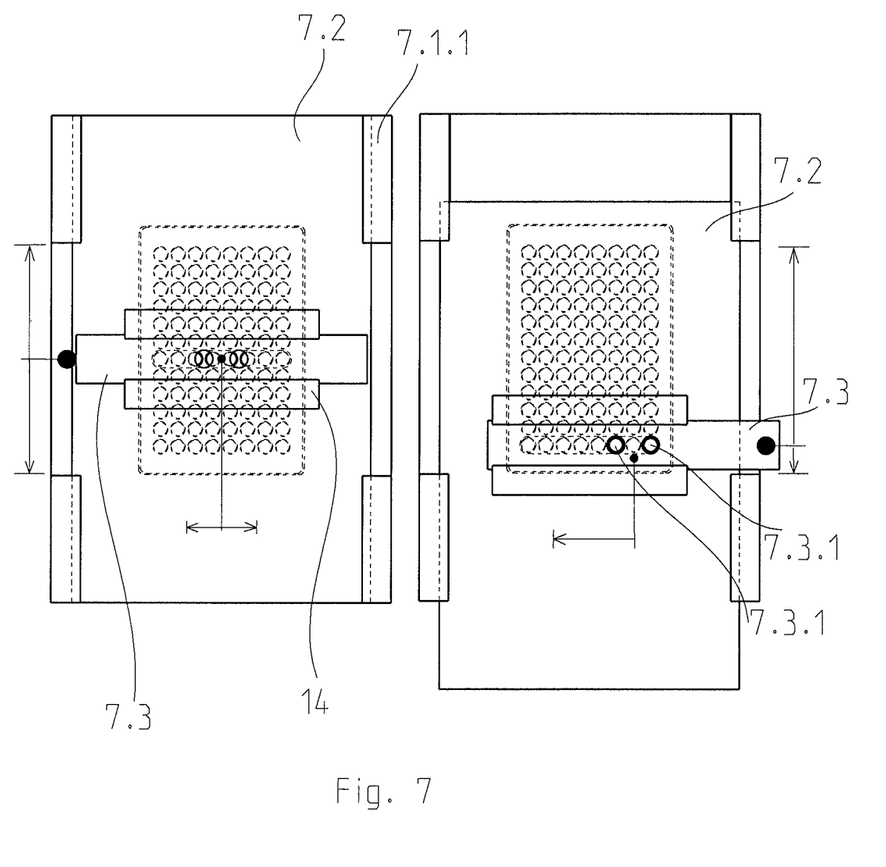
FIG. 7 is a lid part of a cold box according to a fourth embodiment example in two different positions.

According to a fourth embodiment example shown in FIG. 7, the inner lid 7.3 is arranged on the outer lid 7.2 so as to be movable orthogonal to the movement direction of the outer lid 7.2 in guide rails 14. Two through-holes 7.3.1, for example, are provided in the inner lid 7.3.

Figure 8:
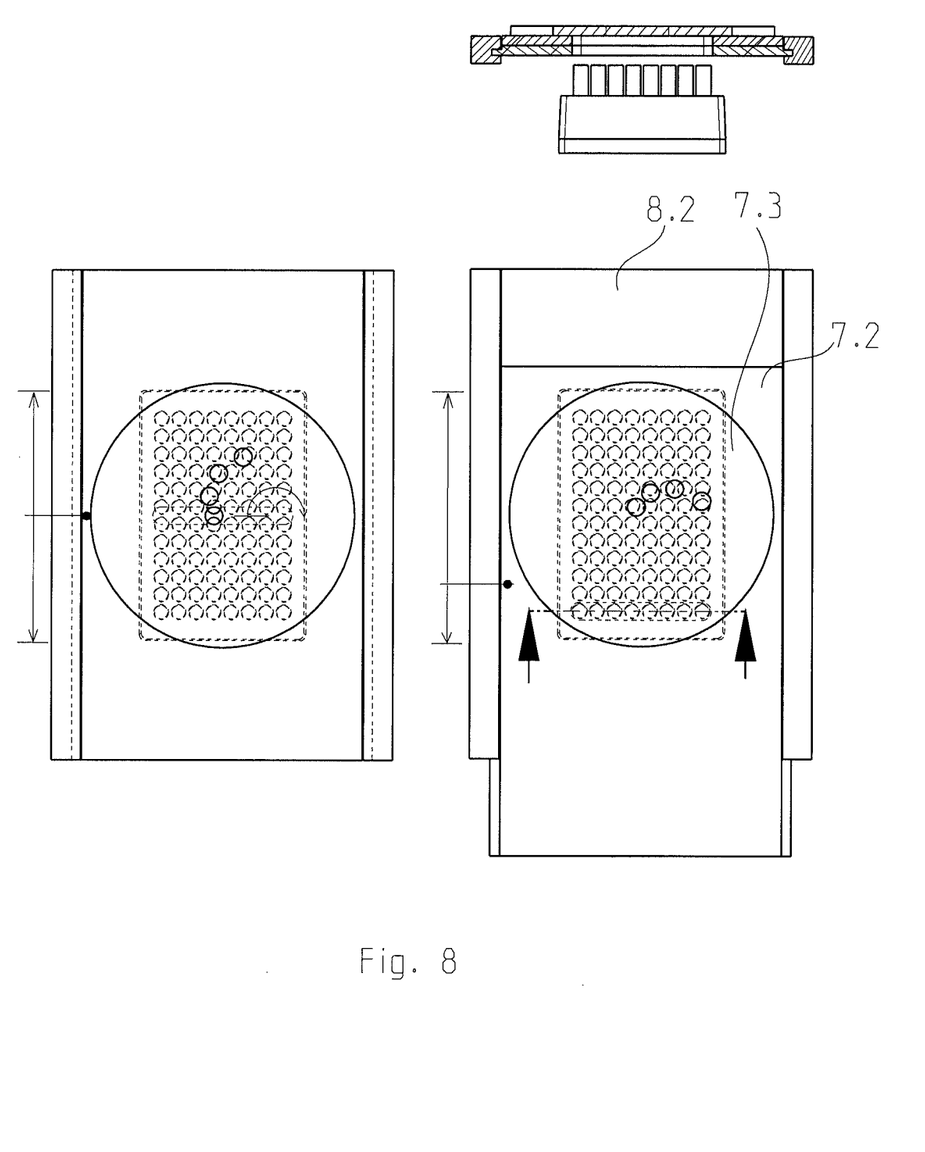
FIG. 8 is a lid part of a cold box according to a fifth embodiment example in two different positions.

In a fifth embodiment example shown in FIG. 8, the inner lid 7.3 is rotatably arranged on the outer lid 7.2. A spiral-shaped arrangement of through-holes 7.3.1 is incorporated in the inner lid 7.3 so as to form an opening 13 when overlapping with a slot-shaped cutout 7.2.1 in the outer lid 7.2, which opening 13 moves in direction of row 3.1 when the inner lid 7.3 is moved relative to the outer lid 7.2. Instead of the arrangement of through-holes 7.3.1, a spiral-shaped slot can also be provided. A large number of further embodiments are possible.

Figure 3A:
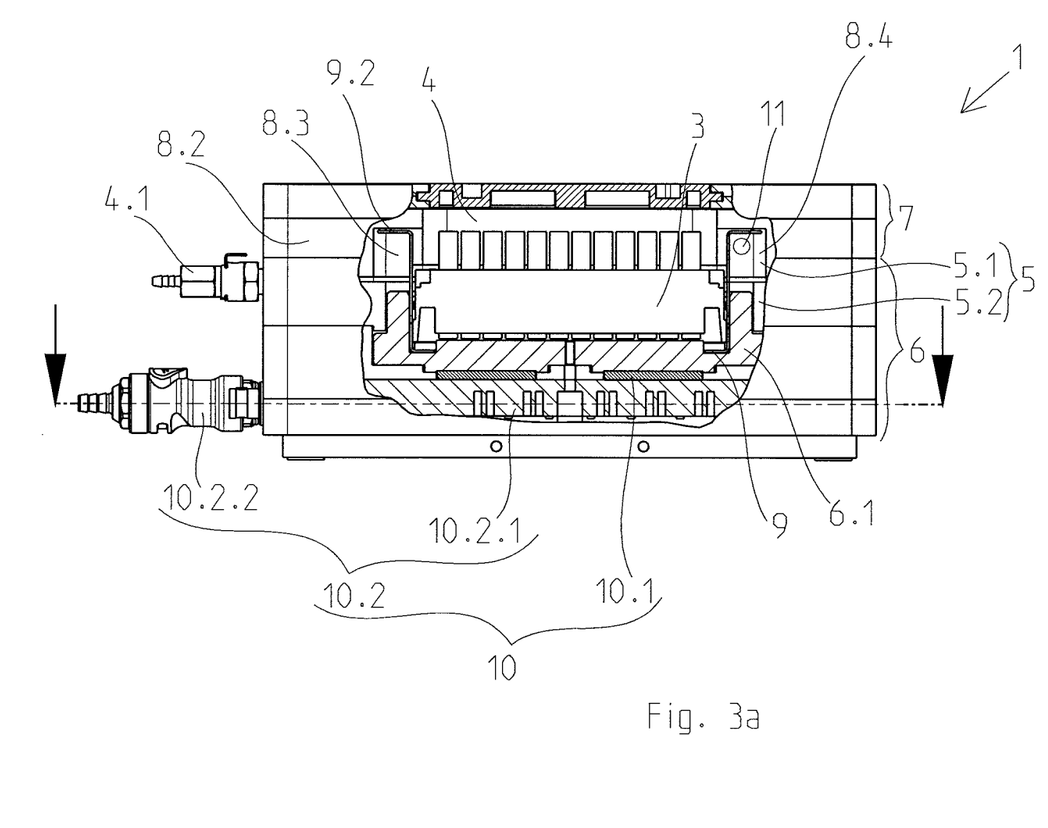
FIG. 3a is a partial section through a side view of a cold box.
Figure 3B:
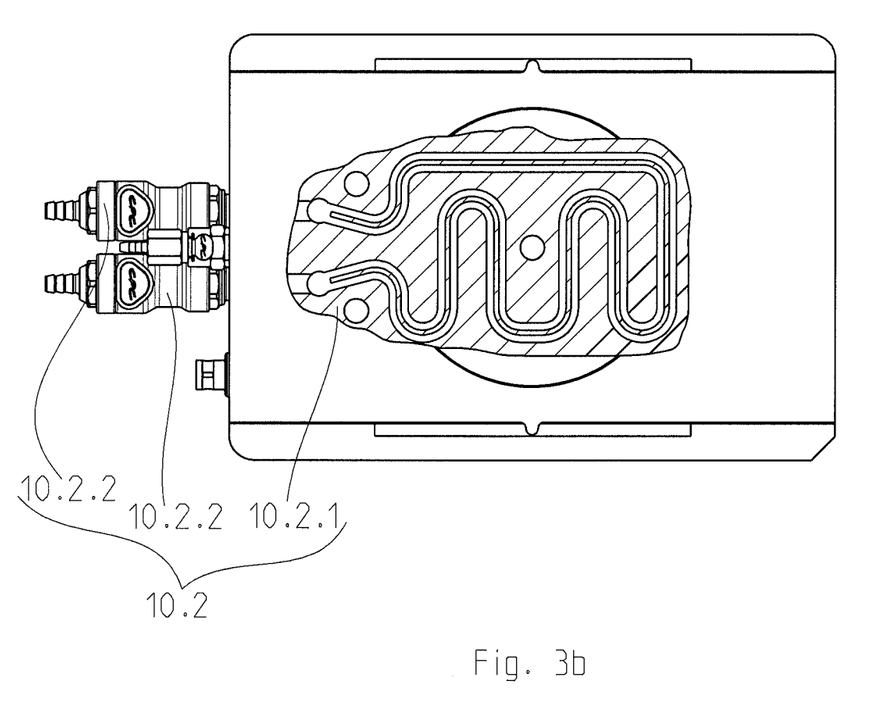
FIG. 3b is a partial section through the top view of a cold box according to FIG. 1.

The cooling device 10 shown in FIGS. 3a and 3b comprises a Peltier cooler 10.1 and a liquid circulating cooler 10.2 and is integrated in the thermal insulation 8 formed by the first shaped body 8.1 such that the Peltier cooler 10.1 contacts the bottom of the trough 6.1 over a large area with its lateral surfaces and accordingly provides for a constant temperature of the trough 6.1 with the aid of a temperature sensor provided in the trough and the control electronics connected thereto. The liquid circulating cooler 10.2 abuts at the opposing (warm) side of the Peltier cooler 10.1 and accordingly acts as a heatsink for the Peltier cooler 10.1. The liquid circulating cooler 10.2 comprises a cooling plate with cooling channels 10.2.1 and connections 10.2.2 which can be connected by a hose system to a heat exchanger or to a laboratory thermostat. Instead of this, the so-called warm side of the Peltier cooler 10.1 could also have a combination of cooling ribs and fans. However, this would not be favorable for automated laboratory installations with respect to evaporation and contamination or noise. Two fold-down handles are advantageously provided at the cooling receptacle 5 for transporting it.

While the invention has been illustrated and described in connection with currently preferred embodiments shown and described in detail, it is not intended to be limited to the details shown since various modifications and structural changes may be made without departing in any way from the spirit of the present invention. The embodiments were chosen and described in order to best explain the principles of the invention and practical application to thereby enable a person skilled in the art to best utilize the invention and various embodiments with various modifications as are suited to the particular use contemplated.

LIST OF REFERENCE NUMERALS 1 cold box
2 tube-shaped vessels
3 rack
3.1 row
3.2 column
4 protective gas
4.1 feed line
5 cooling receptacle
5.1 portion of the cooling receptacle in the lid part 7
5.2 portion of the cooling receptacle in the bottom part 6
6 bottom part
6.1 trough
7 lid part
7.1 lid frame
7.1.1 frame strips
7.2 outer lid
7.2.1 cutout
7.3 inner lid
7.3.1 through-hole
7.3.2 coupling element
8 thermal insulation
8.1 first shaped body
8.2 second shaped body
8.3 formation
8.4 recess
9 tray
9.1 tray bottom
9.2 tray handle
10 cooling device
10.1 Peltier cooler
10.2 liquid circulating cooler
10.2.1 cooling plate with cooling channels
10.2.2 connections
11 gas sensor
12 lid
13 opening
14 guide rails
15 automated pipetting device
16 pipette tip/dispensing needle

What is claimed is:

1. A cold box having a rack loaded with tube-shaped vessels for automated filling by an automated pipetting device, comprising a bottom part and a lid part, a rack which is adapted to be loaded with tube-shaped vessels in a matrix of rows and columns, wherein said rows extend along the width of the rack and said columns extend along the length of the rack, a cooling receptacle enclosed by thermal insulation at least partially arranged in the bottom part and adapted to an outer dimensions of the loaded rack, and in which the loaded rack is placed, said lid part having a lid frame and a lid, said lid being movable in the lid frame in a direction of the columns or rows of the rack and in which is provided a quantity of openings which are adapted to a circumference size of a commercially available pipette tip/dispensing needle of an automated pipetting device so that one of the openings can be positioned over each individual tube-shaped vessel in the rack, said lid completely covering the cooling receptacle in every position so that a dry protective gas with which the cooling receptacle is filled and which is heavier than air remains in the cooling receptacle, and a cooling device which is integrated in the thermal insulation in the bottom part and which contacts the cooling receptacle, wherein the lid is formed of an outer lid with a cutout that reaches at least over the length of a column and an inner lid which is adjustable relative to the outer lid and which covers the cutout, wherein the at least one opening is a though-hole in the inner lid and can be positioned with respect to the tube-shaped vessels by moving the outer lid and adjusting the inner lid.

2. The cold box according to claim 1, wherein the inner lid is integrated in the outer lid.

3. The cold box according to claim 1, wherein the inner lid is round and is rotatable by at least 180° around the geometric center of the outer lid, and the quantity of through-holes is equivalent to one half of the quantity of tube-shaped vessels arranged in a row, wherein the through-holes are arranged on a straight line radial to the center of the outer lid.

4. A cold box having a rack loaded with tube-shaped vessels for automated filling by an automated pipetting device, comprising a bottom part and a lid part, a rack which is adapted to be loaded with tube-shaped vessels in a matrix of rows and columns, wherein said rows extend along the width of the rack and said columns extend along the length of the rack, a cooling receptacle enclosed by thermal insulation at least partially arranged in the bottom part and adapted to the outer dimensions of the loaded rack, and in which the loaded rack is placed, said lid part having a lid frame and a lid, said lid being movable in the lid frame in a direction of the columns or rows of the rack and in which is provided a quantity of openings which are adapted to a circumference size of a commercially available pipette tip/dispensing needle of an automated pipetting device so that one of the openings can be positioned over each individual tube-shaped vessel in the rack, said lid completely covering the cooling receptacle in every position so that a dry protective gas with which the cooling receptacle is filled and which is heavier than air remains in the cooling receptacle, and a cooling device which is integrated in the thermal insulation in the bottom part and which contacts the cooling receptacle, wherein the lid is displaceable in the lid frame proceeding from a central position in positive or negative direction by one half of the length of the rack between two end positions, wherein the length of the lid is selected such that the cooling receptacle remains completely covered by the lid also in the end positions.

* * * * *